United States Patent
Lee et al.

(10) Patent No.: US 12,185,980 B2
(45) Date of Patent: *Jan. 7, 2025

(54) INTEGRATED MULTIPOINT FIXATION SCREW

(71) Applicant: Medos International Sarl, Le Locle (CH)

(72) Inventors: Kevin Lee, Canton, MA (US); Joseph Peterson, South Dartmouth, MA (US)

(73) Assignee: Medos International Sàrl, Le Locle (CH)

( * ) Notice: Subject to any disclaimer, the term of this patent is extended or adjusted under 35 U.S.C. 154(b) by 333 days.

This patent is subject to a terminal disclaimer.

(21) Appl. No.: 17/694,645

(22) Filed: Mar. 14, 2022

(65) Prior Publication Data

US 2022/0296279 A1   Sep. 22, 2022

Related U.S. Application Data

(63) Continuation of application No. 17/174,456, filed on Feb. 12, 2021, now Pat. No. 11,304,728.

(Continued)

(51) Int. Cl.
*A61B 17/70* (2006.01)
*A61B 17/86* (2006.01)
*A61B 17/88* (2006.01)

(52) U.S. Cl.
CPC .......... *A61B 17/70* (2013.01); *A61B 17/8605* (2013.01); *A61B 17/8625* (2013.01); *A61B 17/8685* (2013.01)

(58) Field of Classification Search
CPC . A61B 17/70; A61B 17/7032; A61B 17/8605; A61B 17/8625; A61B 17/8685

(Continued)

(56) References Cited

U.S. PATENT DOCUMENTS 5,039,265 A   8/1991   Rath et al.
5,133,717 A   7/1992   Chopin
(Continued)

FOREIGN PATENT DOCUMENTS

CN   101166477 B   2/2011
CN   102525622 B   4/2016
(Continued)

OTHER PUBLICATIONS

Chinese First Search Report for Application No. 201980034334.1 issued Sep. 25, 2023 (20 pages).

(Continued)

*Primary Examiner* — Eduardo C Robert
*Assistant Examiner* — David C Comstock
(74) *Attorney, Agent, or Firm* — Barnes & Thornburg LLP

(57) ABSTRACT

Bone anchor assemblies and related methods are disclosed herein that can provide for improved fixation of a primary bone anchor. A bone anchor assembly can include a base rotatably received within a rod-receiving member. The base can have a toroid body with a radially-extending portion including at least one auxiliary bone anchor opening that can receive an auxiliary bone anchor to augment fixation of a primary bone anchor of the bone anchor assembly. The base can be rotated relative to the rod-receiving member and the primary bone anchor such that the at least one auxiliary bone anchor opening can be placed in a desired position for supplemental fixation.

19 Claims, 3 Drawing Sheets

Related U.S. Application Data

(60) Provisional application No. 62/976,766, filed on Feb. 14, 2020.

(58) Field of Classification Search
USPC ....... 606/265, 266, 267, 270, 278, 279, 286, 606/305, 308, 319, 328
See application file for complete search history.

(56) References Cited

U.S. PATENT DOCUMENTS

| | | | |
|---|---|---|---|
| 5,147,360 | A | 9/1992 | Dubousset |
| 5,470,333 | A | 11/1995 | Ray |
| 5,582,612 | A | 12/1996 | Lin |
| 5,735,852 | A | 4/1998 | Amrein et al. |
| 5,928,233 | A * | 7/1999 | Apfelbaum ........ A61B 17/7044 606/264 |
| 6,010,503 | A | 1/2000 | Richelsoph et al. |
| 6,342,055 | B1 | 1/2002 | Eisermann et al. |
| 6,524,315 | B1 | 2/2003 | Selvitelli et al. |
| 6,565,569 | B1 | 5/2003 | Assaker et al. |
| 6,585,738 | B1 | 7/2003 | Mangione et al. |
| 6,682,530 | B2 | 1/2004 | Dixon et al. |
| 6,736,820 | B2 | 5/2004 | Biedermann et al. |
| 6,974,460 | B2 | 12/2005 | Carbone et al. |
| 7,179,261 | B2 | 2/2007 | Sicvol et al. |
| 7,232,441 | B2 | 6/2007 | Altarac et al. |
| 7,608,096 | B2 | 10/2009 | Foley et al. |
| 7,618,443 | B2 | 11/2009 | Abdou |
| 7,637,928 | B2 | 12/2009 | Fernandez |
| 7,645,294 | B2 | 1/2010 | Kalfas et al. |
| 7,695,500 | B2 | 4/2010 | Markworth |
| 7,699,876 | B2 | 4/2010 | Barry et al. |
| 7,892,260 | B2 | 2/2011 | Mahoney et al. |
| 7,985,223 | B2 | 7/2011 | Khodadadyan-Klostermann et al. |
| 8,012,184 | B2 | 9/2011 | Schläpfer et al. |
| 8,025,681 | B2 | 9/2011 | Colleran et al. |
| 8,167,917 | B2 | 5/2012 | Chin et al. |
| 8,231,655 | B2 | 7/2012 | Stinson et al. |
| 8,298,269 | B2 | 10/2012 | Null et al. |
| 8,303,631 | B2 | 11/2012 | Duggal et al. |
| 8,343,196 | B2 | 1/2013 | Schneider |
| 8,353,937 | B2 | 1/2013 | Capote et al. |
| 8,454,658 | B2 | 6/2013 | Lindner |
| 8,496,686 | B2 | 7/2013 | Berg et al. |
| 8,506,567 | B2 | 8/2013 | Ziemek et al. |
| 8,551,144 | B2 | 10/2013 | Youssef et al. |
| 8,568,459 | B2 | 10/2013 | Uribe et al. |
| 8,574,268 | B2 | 11/2013 | Chan et al. |
| 8,591,513 | B2 | 11/2013 | Overes et al. |
| 8,758,346 | B2 | 6/2014 | Koay et al. |
| 8,845,697 | B2 | 9/2014 | Montello et al. |
| 8,845,698 | B2 | 9/2014 | Schneider |
| 8,852,245 | B2 | 10/2014 | Schneider |
| 8,876,872 | B2 | 11/2014 | Ziolo et al. |
| 8,876,873 | B2 | 11/2014 | Schneider |
| 8,894,695 | B2 | 11/2014 | Moore et al. |
| 8,979,903 | B2 | 3/2015 | Capote et al. |
| 9,060,815 | B1 * | 6/2015 | Gustine ................ A61B 17/705 |
| 9,962,192 | B2 | 5/2018 | Hawkins et al. |
| 10,238,432 | B2 | 3/2019 | Carruth et al. |
| 10,568,674 | B1 | 2/2020 | Eichenseer |
| 10,779,861 | B2 | 9/2020 | Hawkins et al. |
| 10,898,232 | B2 | 1/2021 | Lee et al. |
| 11,154,332 | B2 | 10/2021 | Hawkins et al. |
| 11,304,728 | B2 * | 4/2022 | Lee ........................ A61B 17/70 |
| 11,426,210 | B2 | 8/2022 | Lee et al. |
| 11,717,327 | B2 | 8/2023 | Lee et al. |
| 11,974,784 | B2 | 5/2024 | Hawkins et al. |
| 11,998,248 | B2 | 6/2024 | Lee et al. |
| 2001/0020169 | A1 | 9/2001 | Metz-Stavenhagen |
| 2001/0047174 | A1 | 11/2001 | Donno et al. |
| 2002/0049446 | A1 | 4/2002 | Harkey, III et al. |
| 2004/0210218 | A1 | 10/2004 | Dixon et al. |
| 2005/0216004 | A1 | 9/2005 | Schwab |
| 2005/0261688 | A1 | 11/2005 | Grady, Jr. et al. |
| 2006/0064091 | A1 | 3/2006 | Ludwig et al. |
| 2006/0195089 | A1 | 8/2006 | LeHuec et al. |
| 2007/0233062 | A1 | 10/2007 | Berry |
| 2008/0140130 | A1 | 6/2008 | Chan et al. |
| 2008/0161858 | A1 | 7/2008 | Mahoney et al. |
| 2008/0183217 | A1 | 7/2008 | Glaser |
| 2008/0234733 | A1 | 9/2008 | Scrantz et al. |
| 2009/0036930 | A1 | 2/2009 | Allison |
| 2009/0125067 | A1 | 5/2009 | Mazzuca et al. |
| 2009/0248077 | A1 | 10/2009 | Johns |
| 2010/0036420 | A1 | 2/2010 | Kalfas et al. |
| 2010/0076496 | A1 | 3/2010 | Fernandez |
| 2010/0094358 | A1 | 4/2010 | Moore et al. |
| 2010/0114174 | A1 | 5/2010 | Jones et al. |
| 2010/0292735 | A1 | 11/2010 | Schlaepfer et al. |
| 2010/0305616 | A1 | 12/2010 | Carbone |
| 2010/0312286 | A1 | 12/2010 | Dell |
| 2011/0184470 | A1 | 7/2011 | Gorek et al. |
| 2011/0230920 | A1 | 9/2011 | Gorek et al. |
| 2011/0288599 | A1 | 11/2011 | Michielli et al. |
| 2012/0010658 | A1 | 1/2012 | Kirschman |
| 2012/0226316 | A1 | 9/2012 | Dant et al. |
| 2013/0046352 | A1 | 2/2013 | McClintock |
| 2013/0053901 | A1 | 2/2013 | Cormier et al. |
| 2013/0060283 | A1 | 3/2013 | Suh et al. |
| 2013/0085534 | A1 * | 4/2013 | Hainard ............. A61B 17/7044 606/278 |
| 2013/0090688 | A1 | 4/2013 | Montello et al. |
| 2013/0096618 | A1 | 4/2013 | Chandanson et al. |
| 2013/0110163 | A1 | 5/2013 | Ballard et al. |
| 2013/0261673 | A1 | 10/2013 | Hawkins et al. |
| 2013/0261679 | A1 | 10/2013 | McBride et al. |
| 2014/0018858 | A1 | 1/2014 | Laeng et al. |
| 2014/0052183 | A1 | 2/2014 | Freese |
| 2014/0081269 | A1 | 3/2014 | Biedermann |
| 2014/0107783 | A1 | 4/2014 | Abdou |
| 2014/0180345 | A1 | 6/2014 | Chan et al. |
| 2014/0188223 | A1 | 7/2014 | Jensen et al. |
| 2014/0249581 | A1 | 9/2014 | Stachniak |
| 2014/0257395 | A1 | 9/2014 | Ledet et al. |
| 2015/0012042 | A1 | 1/2015 | Black |
| 2015/0018889 | A1 | 1/2015 | Schneider |
| 2015/0119940 | A1 | 4/2015 | Jackson et al. |
| 2015/0134016 | A1 | 5/2015 | Biedermann et al. |
| 2016/0000473 | A1 | 1/2016 | Ludwig et al. |
| 2016/0022341 | A1 | 1/2016 | Agarwal |
| 2016/0095637 | A1 | 4/2016 | Elsbury et al. |
| 2016/0106477 | A1 * | 4/2016 | Hynes ................. A61B 17/7032 606/279 |
| 2016/0106479 | A1 | 4/2016 | Hynes et al. |
| 2016/0128732 | A1 | 5/2016 | Strnad et al. |
| 2017/0265901 | A1 | 9/2017 | Hawkins et al. |
| 2017/0348026 | A1 | 12/2017 | Stein et al. |
| 2018/0214185 | A1 | 8/2018 | Hawkins et al. |
| 2018/0228518 | A1 | 8/2018 | Carruth et al. |
| 2019/0038323 | A1 | 2/2019 | Minfelde et al. |
| 2019/0183541 | A1 | 6/2019 | Lee et al. |
| 2019/0254719 | A1 | 8/2019 | Gandhi et al. |
| 2019/0290331 | A1 | 9/2019 | Lee et al. |
| 2020/0030007 | A1 | 1/2020 | Hawkins et al. |
| 2020/0229847 | A1 | 7/2020 | Capote et al. |
| 2021/0085375 | A1 * | 3/2021 | Lee ..................... A61B 17/7059 |
| 2021/0100589 | A1 | 4/2021 | Lee et al. |
| 2021/0251662 | A1 | 8/2021 | Lee et al. |
| 2022/0015806 | A1 | 1/2022 | Hawkins et al. |
| 2022/0370008 | A1 | 11/2022 | Lee et al. |
| 2024/0016521 | A1 | 1/2024 | Lee et al. |
| 2024/0032969 | A1 | 2/2024 | Hawkins et al. |

FOREIGN PATENT DOCUMENTS

| | | |
|---|---|---|
| CN | 107106215 B | 3/2020 |
| CN | 109475371 B | 12/2021 |
| EP | 2266483 A1 | 12/2010 |
| EP | 3429494 A2 | 1/2019 |
| FR | 2951064 A1 | 4/2011 |
| GB | 2483531 A | 3/2012 |
| JP | H04215750 A | 8/1992 |

(56) References Cited

FOREIGN PATENT DOCUMENTS

| | | |
|---|---|---|
| JP | 2001252283 A | 9/2001 |
| JP | 2002512840 A | 5/2002 |
| JP | 2002519135 A | 7/2002 |
| JP | 2010533547 A | 10/2010 |
| JP | 2011502641 A | 1/2011 |
| JP | 2013509952 A | 3/2013 |
| WO | 2013045603 A1 | 4/2013 |
| WO | 2015142320 A1 | 9/2015 |
| WO | 2019180595 A1 | 9/2019 |

OTHER PUBLICATIONS

Chinese Search Report for Application No. 201780030579.8, issued Feb. 5, 2021.
International Search Report and Written Opinion for Application No. PCT/EP2021/052709, mailed Jun. 1, 2021.
Japanese Search Report for Application No. 2018-548909 dated Jan. 28, 2021 (DSP5204).
Japanese Notice of Reasons for Refusal for Application No. 2018-548909, dated Feb. 9, 2021 (DSP5204) (6 pages).
Japanese Decision to Grant a Patent for Application No. 2018-548909 dated Jun. 24, 2021 (DSP5204).
Japanese Search Report for Application No. 2020-550794 dated Jan. 23, 2023 (30 pages).
Japanese Notice of Reasons for Refusal issued for Application No. 2020-550794, dated Feb. 21, 2023 (16 pages).
International Search Report and Written Opinion for Application No. PCT/US2017/022860, mailed Sep. 21, 2017 (20 pages).
International Search Report and Written Opinion for Application No. PCT/IB2019/052191, mailed Jul. 8, 2019 (15 pages).
International Search Report and Written Opinion for Application No. PCT/IB2020/058939, mailed Feb. 5, 2021 (14 bages).
U.S. Appl. No. 18/356,931, filed Jul. 21, 2023, Multipoint Fixation Implants and Related Methods.
U.S. Appl. No. 18/477,163, filed Sep. 28, 2023, Multipoint Fixation Implants.
Chinese Office Action for Application No. 202080067236.0 issued Dec. 21, 2023 (13 pages).
U.S. Appl. No. 17/878,872, filed Aug. 1, 2022, Multipoint Angled Fixation Implants for Multiple Screws and Related Methods.
U.S. Appl. No. 18/647,938, filed Apr. 26, 2024, Multipoint Angled Fixation Implants for Multiple Screws and Related Methods.
Japanese Notice of Reasons for Refusal issued for Application No. 2022-548944 dated Aug. 7, 2024 (7 pages).

* cited by examiner

INTEGRATED MULTIPOINT FIXATION SCREW

CROSS REFERENCE TO RELATED APPLICATION

This application is a continuation of U.S. application Ser. No. 17/174,456, filed on Feb. 12, 2021. U.S. application Ser. No. 17/174,456 claims the benefit of U.S. Provisional Application No. 62/976,766, filed on Feb. 14, 2020. Each of these applications is hereby incorporated by reference in its entirety.

FIELD

Orthopedic implants and related methods are disclosed herein. For example, bone anchor assemblies with multiple bone engagement points are disclosed.

BACKGROUND

Bone anchor assemblies can be used in orthopedic surgery to fix bone during healing, fusion, or other processes. In spinal surgery, for example, bone anchor assemblies can be used to secure a spinal fixation element to one or more vertebrae to rigidly or dynamically stabilize the spine. Bone anchor assemblies can also be used as an engagement point for manipulating bone (e.g., distracting, compressing, or rotating one vertebra with respect to another vertebra, reducing fractures in a long bone, and so forth).

The integrity with which the bone anchor assembly engages the bone can affect the transfer of corrective biomechanical forces. While a great amount of care is exercised when placing bone anchor assemblies, it is common that a bone anchor assembly will be inserted in a compromised state. For example, the bone opening in which the assembly is disposed can be stripped (e.g., by driving the bone anchor assembly past its optimum holding position), the bone anchor assembly can be placed incorrectly (e.g., using an incorrect instrument maneuver such as an over-sized pilot hole), the bone anchor assembly can be placed outside of its intended trajectory (e.g., within a facet capsule or breached through a pedicle wall), or the bone anchor can be inserted into compromised bone (e.g., bone that is fractured, osteoporotic, diseased, or otherwise lacking in structural integrity).

When the bone anchor assembly is in a compromised state, there can be sub-optimal purchase between the bone anchor assembly and the bone. The bone anchor assembly may feel unsecure to the surgeon, and it is possible that the bone anchor assembly could back out or become loosened over time. There are limited options for the surgeon when faced with these types of situations. In spinal surgery, for example, the surgeon can remove the bone anchor assembly and skip the vertebral level, though this can undesirably require expanding the surgical site to additional vertebral levels. The surgeon can remove and re-insert with a larger anchor, though this may not be an option when space for anchoring in the bone is limited. The surgeon can leave the compromised bone anchor assembly in place, which may be the safest alternative if the bone anchor assembly is in a safe location and attachment to the plate, rod, or other implant construct is definitive, as the additional compromised fixation may be better than removal.

Even when a bone anchor assembly is placed in a non-compromised state, the geometry of traditional bone anchor assemblies can limit the flexibility with which the bone attachment point can be located with respect to a plate, rod, or other implant construct coupled to the bone anchor assembly.

There is a continual need for improved bone anchor assemblies and related methods.

SUMMARY

Bone anchor assemblies are disclosed herein that can provide for improved fixation as compared with traditional bone anchor assemblies. An embodiment of an assembly can include a multipoint eyelet component that is part of a bone anchor base. The eyelet component can be integrated into a receiver member assembly in a manner that allows positioning the eyelet at any desired position around a circumference of the receiver member. The eyelet component can accommodate one or more auxiliary bone anchors that augment the fixation of the assembly's primary bone anchor. Surgical methods using the bone anchor assemblies described herein are also disclosed.

In one aspect, a bone anchor assembly can include a base, a receiver member, and a shank. The base can include a toroid body portion and a radial protrusion (e.g., an eyelet or wing) extending radially from the toroid, the radial protrusion having at least one auxiliary bone anchor opening configured to receive an auxiliary bone anchor. The receiver member can have a proximal end, a distal end, a lumen extending from the proximal end to the distal end, and a rod-receiving recess. The shank can have a head portion retained within the toroid body of the base and a bone engaging portion that extends distally from the base. The base can be coupled to the receiver member such that the base is configured to rotate relative to the receiver member.

The devices and methods described herein can have a number of additional features and/or variations, all of which are within the scope of the present disclosure. In some embodiments, for example, the toroid body of the base can extend distally from the receiver member. The base can include an extension that can extend proximally from the toroid body. The extension can be received within a lumen of the receiver member. In some such embodiments, the extension can have a first connection feature and the receiver member can have a second connection feature. The first connection feature can be configured to engage with the second connection feature such that the base can be rotatably received within the receiver member. Further, in some embodiments, the first connection feature and the second connection feature can be configured such that relative axial movement between the base and the receiver member can be restricted when the first connection feature engages with the second connection feature. In some embodiments, the first connection feature can be a lip at a proximal end of the extension, and the second connection feature can be a groove in an inner surface of the receiver member. The groove of the receiver member can be distal to the rod-receiving recess.

In some embodiments the bone anchor assembly can include a saddle disposed within the receiver member. The saddle can have a distal-facing surface that can contact a proximal-facing surface of the extension of the base when the base is disposed within the receiver member. In some embodiments, the at least one auxiliary bone anchor opening of the radially-extending portion can include a plurality of auxiliary bone anchor openings. A central lumen of the at least one auxiliary bone anchor opening can extend at a transverse angle relative to a central axis of the receiver member. The central lumen of the at least one auxiliary bone anchor opening can be angled in one of a caudal and a cephalad direction. In some embodiments, the central lumen of the at least one auxiliary bone anchor opening can be angled in one of a medial and a lateral direction.

In another aspect, a surgical method can include driving a shank portion of a bone anchor into a bone of a patient and rotating a base of a bone anchor assembly relative to a receiver member of the bone anchor assembly, the base having a radially protruding portion with at least one auxiliary bone anchor opening extending therethrough and the receiver member configured to receive a spinal fixation element. The method can include positioning the radially protruding portion of the bone anchor at a desired position relative to the shank portion and driving at least one auxiliary bone anchor through the at least one auxiliary bone anchor opening and into bone of the patient.

In some embodiments, driving the at least one auxiliary bone anchor through the at least one auxiliary bone anchor opening and into bone of the patient can include driving the at least one auxiliary bone anchor through the at least one auxiliary bone anchor opening with an insertion trajectory that can be biased relative to at least one of a central axis of the receiver member and the shank to supplement fixation of the bone anchor within the bone. Rotating the base of the bone anchor assembly can include rotating the base about a central longitudinal axis of the receiver member.

In some embodiments the method can include placing a spinal rod within the receiver member and securing the spinal rod within the receiver member before driving the at least one auxiliary bone anchor into bone. In other embodiments, placing a spinal rod within the receiver member and securing the spinal rod within the receiver member can occur after driving the at least one auxiliary bone anchor into bone.

The method can further include assembling the bone anchor by coupling the base to the receiver member such that the base is rotatable with respect to a central longitudinal axis of the receiver member and inserting the shank through the receiver member and the base such that a distal bone-engaging portion of the shank extends distally from the base and a head portion of the shank is received within the base. In some embodiments, the shank can be polyaxially rotatable relative to the base.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The aspects and embodiments of the present disclosure described above will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices, systems, and methods disclosed herein. One or more of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure.

Bone anchor assemblies are disclosed herein that can provide for improved fixation as compared with traditional bone anchor assemblies. A bone anchor assembly of the present disclosure can include a primary screw shank to engage with bone, a base having a radially-extending protrusion (e.g., a protruding eyelet, wing, etc.) with at least one auxiliary bone anchor opening to receive an auxiliary bone anchor, and a receiver member for receiving a spinal fixation element. The base can couple with the receiver member such that the base can rotate relative to, and independently of, the receiver member and primary shank. In this manner, the base can be rotated to adjust the positioning of the one or more auxiliary bone anchor openings relative to the receiver member and bone anchor once the primary screw shank has engaged with bone, e.g., a vertebra, of a patient.

The bone anchor assembly can be assembled by inserting the screw shank into the base such that a proximal head of the screw shank can be seated or otherwise retained within the base with a distal bone-engaging portion of the screw shank extending distally from the base. The base can be inserted into the receiver member and coupled therewith such that the base can rotate relative to the receiver. The screw shank can be driven into patient anatomy, e.g., a vertebra, and the base can be rotated freely about a longitudinal axis of the receiver member to position one or more auxiliary bone anchor openings on a protrusion (e.g., an eyelet, wing, etc.) of the base at a desired location for supplemental fixation, i.e., fixation beyond that provided by the primary screw shank. One or more auxiliary bone anchors, also referred to herein as supplemental fixation screws, can be inserted into the auxiliary bone anchor openings and driven to engage with patient anatomy to provide the desired supplemental fixation. A spinal fixation rod can be placed and/or secured within the receiver member either before or after placement of the supplemental fixation screws. Accordingly, bone anchor assemblies of the present disclosure can provide supplemental fixation to a primary screw in a strategic and patient-specific manner, without requiring additional components beyond the bone anchor assembly.

Figure 1:
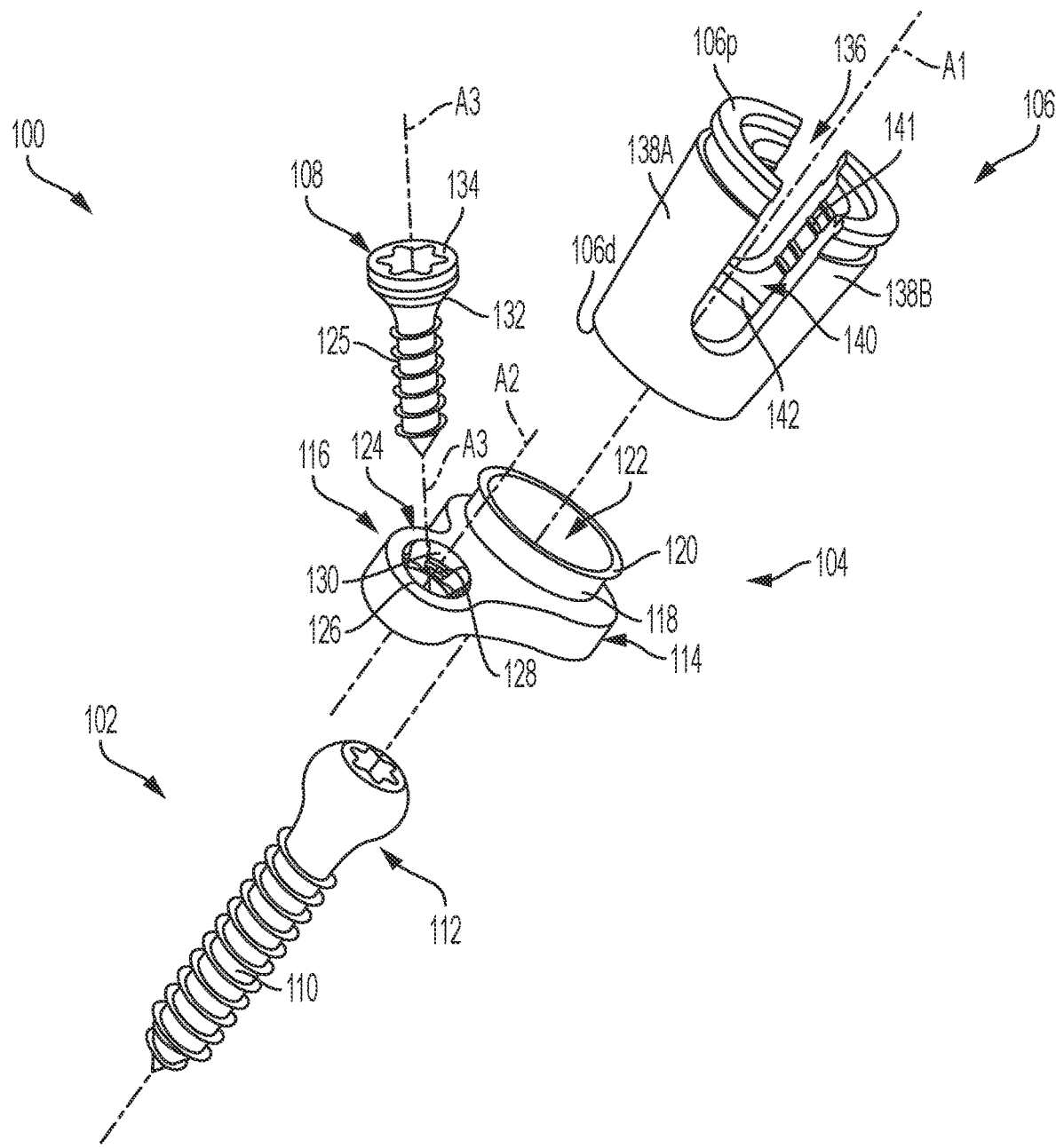
FIG. 1 is an exploded perspective view of one embodiment of a bone anchor assembly of the present disclosure.

FIG. 1 illustrates an exploded view of one embodiment of a bone anchor assembly 100 in accordance with the present disclosure. As noted above, a bone anchor can sometimes be inserted in a compromised state. This can be undesirable, especially in instances in which there is limited bone area in which to install additional bone anchors. The illustrated bone anchor assembly 100 can allow for supplemental fixation of a primary bone anchor in a compact footprint, without necessarily requiring removal or re-insertion of the primary bone anchor. As shown, the bone anchor 100 can include a primary bone anchor 102, also referred to as a primary screw shank, a base 104, a receiver member 106 for receiving a spinal fixation element (not shown), such as a spinal rod, to be coupled to the bone anchor, and one or more auxiliary bone anchors 108. A closure mechanism (not shown), such as a set screw, can capture a spinal fixation element within the receiver member 106 and fix the spinal fixation element with respect to the receiver member. The spinal fixation element, e.g., the spinal rod, can either directly contact the receiver member 106 (or other component such as base 104 and/or bone anchor 102, or can contact an intermediate element, e.g., a saddle 105, as shown, for example, in FIGS. 2 and 3. In use, the base 104 can be coupled to the receiver member 106 such that the base can rotate relative to the receiver member about a central longitudinal axis A1 of the receiver member, while relative movement along the longitudinal axis A1 can be restricted or limited. One or more supplemental fixation screws 108 can be driven into bone through a corresponding one or more auxiliary bone anchor openings 124 of the base 104 and can supplement fixation of the bone anchor 102 within patient anatomy.

The primary screw shank 102 can include a distal threaded shaft 110 configured to engage bone and a proximal head 112. The proximal head 112 can generally have the shape of a truncated sphere with a planar proximal surface and an approximately spherically-shaped distal surface. The proximal head 112 of the screw shank 102 can engage with a distal end of the base 104, for example, in a ball and socket like arrangement in which the proximal head 112 can pivot relative to the base 104. A distal surface of the proximal head 112 of the shank 102 and a mating surface within the distal end of the base 104 can have any shape that can facilitate this arrangement, including, for example, spherical, toroidal, conical, frustoconical, and any combination thereof.

The distal shaft 110 of the shank 102 can be configured to engage bone and, in the illustrated embodiment, can include an external bone engaging thread. The thread form for the distal shaft 110, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein.

The base 104 can have a toroid body portion 114 with a radially protruding portion (e.g., an eyelet or wing) 116 extending radially therefrom. An extension 118 can extend proximally from the toroid body 114. The proximal extension 118 can include a lip 120, or other connection feature, such as, for example, one or more prongs, a groove, etc., for engagement with a complimentary connection feature of the receiver 106. In some embodiments the extension 118 and the lip 120 can be deformable. For example, the lip 120 can compress radially inward when the lip 120 is received within a lumen 136 of the receiver member 106, and can expand radially outward from a compressed position when the lip 120 aligns with a groove 142 of the receiver member. In this manner, the lip 120 of the base 104 can engage with the groove 142 of the receiver member 106 to retain the base 104 within the receiver member 106. In some embodiments the lip 120 and the extension 118 can be a deformable monolithic structure. In other embodiments, a connection feature, e.g., the lip 120, can be formed on or extend from the toroid body 114 itself, and the proximal extension 118 can be omitted.

A lumen 122 with a central longitudinal axis A1 can extend through the base 104, and, more particularly, can extend through the toroid body 114 and the proximal extension 118 (the central longitudinal axis A1 of the lumen 122 may also be referred to as the central longitudinal axis A1 of the base 104). The screw shank 102 can be inserted through the lumen 122 such that the distal threaded portion 110 extends distally from the toroid body 114 while the head portion 112 of the screw shank 102 can be received within the toroid body 114. In some embodiments, an interior surface of the toroid body 114 can include features complementary to the proximal head 112 of the screw shank 102 such that the screw shank can be retained within the toroid body 114 and, in some embodiments, can move polyaxially relative to the toroid body. While a "top-down" assembly is described above, wherein the screw shank 102 is passed distally through the base 104 until the proximal head 112 is received within the toroid body 114 of the base, in other embodiments the assembly can be configured for "bottom loading," wherein the screw shank 102 is passed proximally through the base 104 in order to seat the proximal head 112 into the toroid body 114. This can be accomplished, for example, by forming the toroid body 114 and/or proximal head 112 such that it can deform to allow passage of the proximal head into a recess of the toroid body. Examples of features permitting such coupling can include the use of elastically deformable materials, elastic fingers forming a collet or other gripping structure, etc.

The protruding portion or wing 116 can extend from the toroid body 114 and can form part of the base 104. The protruding portion 116 can extend radially outward from the toroid body 114, i.e., away from the central longitudinal axis A1 of the lumen 122. An auxiliary bone anchor opening 124 can be formed in the wing 116. While a single opening 124 is shown extending through the wing 116 of FIG. 1, in some embodiments, the wing 116 can include a plurality of auxiliary bone anchor openings 124. The auxiliary bone anchor opening 124 can be configured to receive an auxiliary fixation element 108. As shown in FIG. 1, a central longitudinal axis A2 of the opening 124 can extend substantially parallel to the central longitudinal axis A1 of the lumen 122. In other embodiments, the opening 124 can extend with a biased or angled trajectory relative to the central axis A1 of the lumen 122. For example, the central axis A2 of the opening 124 can extend at an oblique angle relative to the central longitudinal axis A1 of the lumen 122. In this manner, an auxiliary bone anchor 108 can be received through the auxiliary bone anchor opening 124 and can be placed within patient anatomy with a caudal or cephalad trajectory, depending on placement of the protruding portion 116 relative to the patient anatomy. Additionally, or alternatively, the central axis A2 of the opening 126 can extend radially inward towards the central axis A1 of the opening 122 or radially outward away from the central axis A1 of the opening 122. In embodiments with a plurality of auxiliary bone anchor openings 124 in the protruding portion 116, each opening 124 can be angled or biased to have either the same or different trajectories. Further features and embodiments of an auxiliary bone anchor opening can be found in U.S. Patent Application Publication No. 2021/0085375, filed on Sep. 25, 2019, entitled "Multipoint Angled Fixation Implants for Multiple Screws and Related Methods," the entire contents of which are hereby incorporated by reference.

In some embodiments, each auxiliary bone anchor opening 124 can include any of a number of features for accepting an auxiliary bone anchor 108 at varying angles, such as, for example, conical, spherical, or parabolic threads. For example, as discussed in U.S. Patent Application Publication No. 2021/0085375 with respect to, for example, FIGS. 2A-2M, the opening 124 can be at least partially threaded to receive a variable-angle locking screw 108 having a threaded proximal head 132. As shown in FIG. 1, the opening 124 can have a plurality of columns of threads 128 spaced apart to define a plurality of non-threaded recesses 130. In this manner, the threads of the opening 124 can form an interlocking interface and mate with threads 125 of the supplemental fixation screw 108 to lock the screw 108 therein. In one embodiment, the threads of the opening 124 can be conical threads. The columns of threads 128 can be arranged around an inner surface of the opening 124 for engaging threads 132 on a head of a locking and/or a variable-angle auxiliary bone screw 108. The supplemental fixation screw 108 can thus be locked within the protruding portion 116, and specifically within the opening 124, co-axially with the central axis A1 of the base 104 or at a selected angle within a range of selectable angles relative to the central axis of the base. For example, the screw 108 can be inserted into the opening 124 along a trajectory A3 that can extend at a transverse angle relative to the central axis A2 of the opening. The opening 124 can have any number of columns of threads 128 (e.g., two, three, four, etc.) to facilitate variable angle locking with the supplemental fixation screw 108. Additionally, or alternatively, the opening 124 can include one or more additional locking components, such as a cam, and/or can facilitate locking with the screw 108 through material deformation, e.g., splaying of the auxiliary bone anchor opening.

The auxiliary bone anchor 108 can include features to facilitate this variable-angle locking, such as a proximal head that is at least partially spherical having a thread with a profile that follows the arc-shaped radius of curvature of the spherical portion of the head. The variable-angle capability of the interlocking interface (i.e., the screw/opening interface) can allow the user to place a locking auxiliary bone anchor into the bone at any angle defined within angulation limits, thus providing improved placement flexibility and eliminating or reducing the need to conform the wing 116 to a bone surface to achieve a desired insertion angle. Accordingly, the auxiliary bone anchor 108 can be driven into the bone with a diverging or converging longitudinal axis relative to the primary bone anchor 102. In instances in which a plurality of bone anchors 108 can each be driven through an opening of the protruding portion 116, the bone anchors 108 can be driven into the bone with diverging or converging longitudinal axes relative to each other and/or relative to the primary bone anchor 102. Biased or angled trajectories of the auxiliary bone anchors 108 can provide improved resistance to pullout. A locking interface between an auxiliary bone anchor opening and an auxiliary bone anchor can increase stability and prevent the auxiliary bone anchor from backing out of the opening.

As described above, the auxiliary bone anchor opening 124 can include a locking interface with one or more locking features to lock a head of the auxiliary bone anchor within the opening 124. In other embodiments, the opening 124 can have a lagging interface with the auxiliary bone anchor, in which the head of the auxiliary bone anchor does not independently lock relative to the opening 124. In some such embodiments, the interior surface of the opening 124 can be smooth or spherical, without threads or locking features.

The receiver member 106 can have a proximal end 106p, a distal end 106d, and a lumen 136 extending therebetween. The proximal end 106p can have a pair of spaced apart arms 138A, 138B defining a U-shaped rod-receiving recess 140 therebetween for receiving a spinal fixation element, e.g., a spinal rod. Each of the arms 138A, 138B can extend from the distal end 106d of the receiver member 106 to a free end. The outer surfaces of each of the arms 138A, 138B can include a feature, such as a recess, dimple, notch, projection, or the like, to facilitate connection of the receiver member 106 to instruments. For example, the outer surface of each arm 138A, 138B can include an arcuate groove at the respective free end of the arms. Such grooves are described in more detail in U.S. Pat. No. 7,179,261, issued on Feb. 20, 2007, which is hereby incorporated by reference herein. A closure mechanism, such as a set screw, (not shown) can be positioned between and can engage the arms 138A, 138B to capture a spinal fixation element, e.g., a spinal rod, (not shown) within the receiver member 106 and fix the spinal fixation element with respect to the receiver member. For example, the arms 138A, 138B can have internal threads 141 that can engage with external threads of the closure mechanism.

The distal end 106d of the receiver member 106 can have a distal end surface which is generally annular in shape defining an opening through which at least a portion of the base 104 and the shank 102 can extend. For example, the extension 118 of the base 104 can be inserted through the distal opening of the receiver member 106 such that the lip 120 of the extension can engage with the groove 142 of the receiver member and the toroid body 114 of the base can extend distally from the receiver member. As described in detail with reference to FIGS. 2-4, the base 104 can couple with the receiver member 106 such that the base can be rotated relative to the receiver member about a central longitudinal axis of the receiver member.

In the assembled configuration of the bone anchor assembly 100, a central longitudinal axis of the lumen 136 of the receiver member 106 can be co-axial with the central longitudinal axis A1 of the lumen 122 of the base. The base 104 can couple with the receiver member 106 such that the base 104 can rotate about the central axis A1 relative to the receiver member. In some embodiments, the base 104 can rotate 360 degrees about the central axis A1 relative to the receiver member in both a clockwise or counter-clockwise direction. Relative axial movement along the central axis A1 between the base 104 and the receiver member 106, however, can be limited or restricted. The receiver member 106 can receive a spinal fixation element, such as a spinal rod (not shown), within the rod-receiving recess 140 such that the spinal fixation element can extend transverse relative to the longitudinal axis A1.

Figure 2:
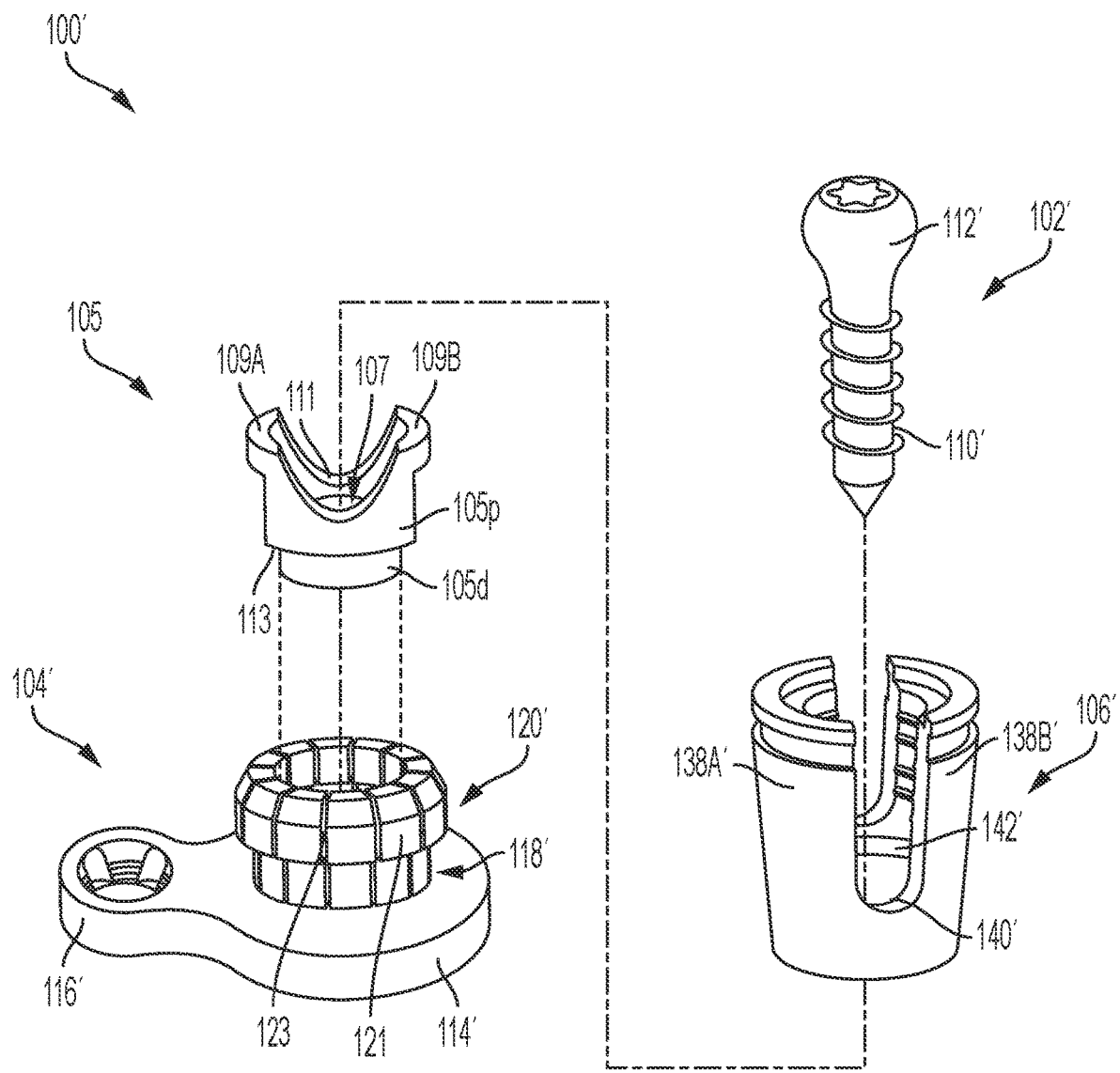
FIG. 2 illustrates an exploded perspective view of another embodiment of a bone anchor assembly of the present disclosure.
Figure 3:
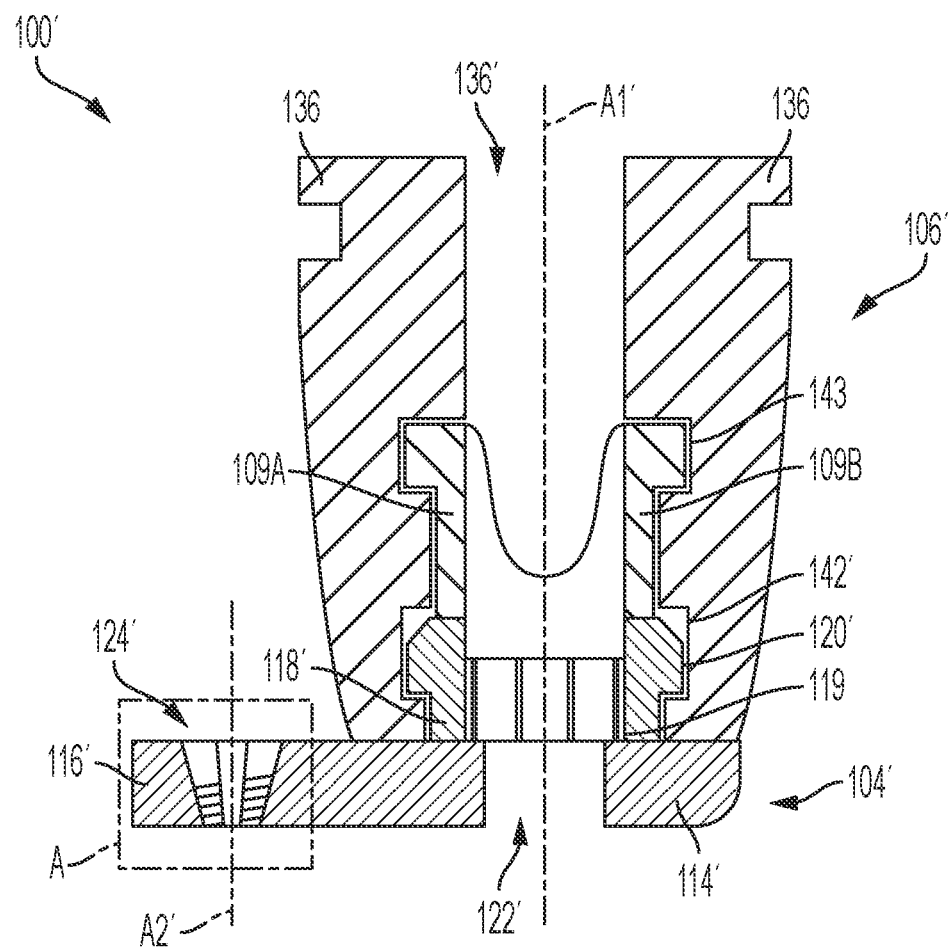
FIG. 3 is a cross-sectional view of the bone anchor assembly of FIG. 2.

The structure, assembly, and use of bone anchor assemblies of the present disclosure will now be described in greater detail with reference to the alternative embodiment of a bone anchor assembly 100' as shown in FIGS. 2 and 3. FIG. 2 shows an exploded perspective view of the bone anchor assembly 100', and FIG. 3 shows a cross-sectional view of the assembled bone anchor of FIG. 2. Except as described herein or as will be readily appreciated from the present disclosure, the bone anchor assembly 100' can be substantially similar to the bone anchor assembly 100 described above, with like-numbered components generally having similar features. In use, the base 104' can be received within the receiver member 106' such that the toroid body 114' can extend distally from the receiver member and the base can rotate relative to the receiver. Optionally, a saddle 105 can be interposed between the base 104' and a spinal fixation element (not shown) received within the receiver member 106'. The head 112 of the shank 102 can be received within the base 104', while the distal shaft 110 of the shank can extend distally from the base and, accordingly, from the receiver member 106', to engage with bone. The protruding portion 114' can be rotated relative to the receiver 106' and can be positioned such that the one or more auxiliary bone anchor openings 124' can be strategically located relative to the shank 102 and patient anatomy to provide the desired supplemental fixation. One or more auxiliary bone anchors can be driven through the one or more auxiliary bone anchor openings in the protruding portion of the base to engage with bone and provide supplemental fixation support to that of the primary bone anchor.

The lip 120' of the base 104' can be received within the groove 142' of the receiver member 106' such that the base 104' can rotate relative to the receiver member 106' about the axis A1. Relative axial movement, i.e., movement along the axis A1, however, can be restricted, for example, by tolerance dimensions of the groove 142' relative to the lip 120' and/or a length of the extension 118' of the base 104' along the direction of the axis A1. In some embodiments, the extension 118' and the lip 120' can include one or more deformable fingers 121 with gaps 123 therebetween. The fingers 121 can compress radially inward when received within the lumen 136' of the receiver member 106', and can expand outward when the lip 120' aligns with the groove 142' of the receiver member. While the embodiments illustrated in FIGS. 1-3 show a connection feature of the base 104, 104' as the lip 120, 120' and a complementary connection feature of the receiver member 106, 106' as the groove 142, 142' alternative complementary connection features can be used and are within the scope of the present disclosure, so long as the connection between the base and the receiver member allows for relative rotation therebetween. By way of non-limiting example, a groove or one or more prongs can be formed on an interior distal surface of the receiver member 106 and can engage with a groove formed on an external surface of the extension 118.

FIG. 3 shows the base 104' and the saddle 105 received within the receiver member 106'. At least a portion of the extension 118' of the base 104' can be received within a distal portion of the lumen 136' of the receiver member 106' such that the toroid body 114' of the base extends distally from the distal surface of the receiver member. As discussed above, the lip 120' of the extension 118' can be deformable, and can compress radially inward during insertion of the extension into the receiver member 106'. The lip 120' can then expand to its initial state when the lip aligns with the groove 142' of the receiver member 106', as shown in FIG. 3, and can retain the base 104' within the receiver member. A proximal facing surface of the toroid body 114' can contact a distal-facing surface of the receiver member 106'. In other embodiments, a portion of the extension 118' can extend distally from the receiver member 106' such that the toroid body 114' does not contact the receiver member 106'. As described above, the wing 116' can extend from the toroid body 114' radially outward from the central axis A1, i.e., radially outward relative to the lumen 122 of the base 104'. In the assembled configuration, the wing 116', having at least one auxiliary bone anchor opening 124', can rotate with the base 104' relative to the receiver member 106'.

The saddle 105 can be received within the lumen 136' of the receiver member 106', with at least a portion of the saddle in contact with the base 104'. The saddle 105 can have a proximal portion 105p, a distal portion 105d, and a lumen 107 extending therebetween. The saddle 105 can include a pair of spaced apart arms 109A, 109B defining a U-shaped seat 111 that can receive the spinal fixation element, and a distal-facing surface 113 of the proximal portion 105p that can abut a proximal-facing surface of the base 104' and/or a portion of the proximal head 112 of the screw shank 102. The distal portion 105d of the saddle 105 can be received within the extension 118' of the base 104' such that the distal portion of the saddle can extend into the lumen 122 of the base. The saddle 105 can be positioned within the receiver member 106' and interposed between the base 104 and a spinal fixation element in the rod-receiving recess 140. For example, the saddle 105 can be inserted into the lumen 136 of the receiver member 106 such that the arms 109A, 109B deflect radially inward. As the saddle 105 advances to a position where a distal portion of the arms 109A, 109B align with a groove 143 formed in the receiver member 106, the arms can expand radially outward to seat portions thereof within the groove 143, thereby retaining the saddle to the receiver member. Dimensions of the groove 143 and portions of the arms 109A, 109B configured to be received therein can be set to allow for desired axial movement of the saddle 105 relative to the receiver member 106 when, e.g., varying forces exerted by the saddle on the shank 102. More particularly, with the proximal head 112 of the shank 102 received within the base 104', the saddle 105 can compress a distal outer surface of the head of the shank 102 into direct, fixed engagement with a distal inner surface 119 of the base 104'. The head 112 of the shank 102 can be received and retained within the base 104', i.e., within the lumen 122', while the distal shaft 110 of the shank can extend distally from the toroid body 114' of the base 104'. The shank 102 can be inserted into the base 104' before or after inserting the base 104' into the receiver member 106'.

Figure 4:
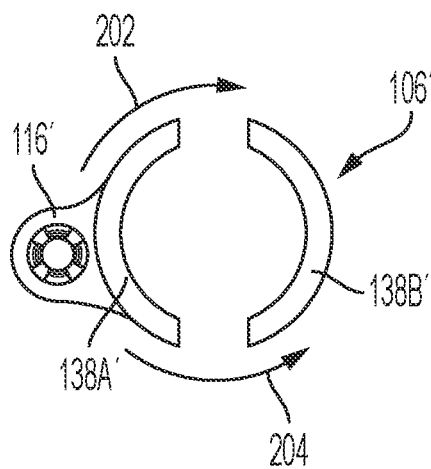
FIG. 4 schematically illustrates a top view of the base of the bone anchor assembly of FIG. 2 in a first position relative to a receiver of the bone anchor assembly of FIG. 2.
Figure 5:
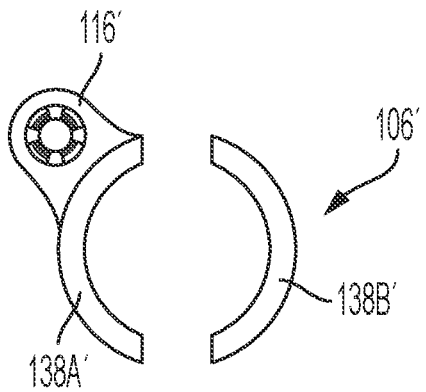
FIG. 5 schematically illustrates a top view of the base of the bone anchor assembly of FIG. 2 rotated to a second position relative to the receiver of the bone anchor assembly of FIG. 2.

In the assembled configuration, the base 104' can rotate 360 degrees relative to the receiver 106'. For example, FIG. 4 shows a top view of a first position of the base 104' with respect to the receiver member 106', in which the wing 116' can extend to the left of the receiver, with respect to the illustrated view in FIG. 4, at substantially a mid-line of the receiver arm 138A'. The base 104' can be rotated relative to the receiver 106' in either a clockwise or counter-clockwise direction, indicated by arrows 202 and 204, respectively. For example, a user can grasp the wing 116' or toroid body 114' and rotate the base 104' clockwise to place the wing 116' in a second position, for example the position shown in FIG. 5, that is different from the first position.

One embodiment of a method of use of the bone anchor assembly 100 will now be described. The bone anchor assembly 100 can be assembled prior to implantation into a patient. The screw shank 102 can be top-loaded into the base 104. More particularly, the screw shank 102 can be passed distally through the lumen 122 of the base 104 such that the shaft 110 of the screw shank can extend distally from the toroid body 114 of the base while the proximal head 112 of the screw shank can be received within the lumen 122 of the base 104. Alternatively, in some embodiments, the screw shank 102 can be bottom-loaded into the base 104.

The base 104 with the shank 102 received therein can be inserted into the receiver 106 such that the base can be rotated relative to the receiver. More particularly, the extension 118 can be inserted through the distal opening of the receiver 106 and can be moved proximally within the lumen 136 of the receiver until the lip 120 of the base 104 can be captured, e.g., within the groove 142 of the receiver 106. Alternatively, the base 104 can be coupled to the receiver 106 prior to inserting the shank 102 through the base 104. In such instances, the shank 102 can be moved distally through the lumen 136 of the receiver 106 and the lumen 122 of the base 104. In some embodiments, the base 104 and the receiver member 106 can be manufactured as a single component with the base rotatable relative to the receiver member 106 as described herein. As discussed above, with the base 104 connected with the receiver 106, the base, including the toroid body 114 and the wing 116, can rotate relative to, and independently of, the receiver 104 about the central axis A1.

With the receiver member 106, the base 104, and the screw shank 102, i.e., the primary bone anchor, assembled, the shank can be driven into bone in accordance with standard surgical technique. For example, the bone anchor assembly 100 can be a polyaxial bone screw designed for posterior implantation in the pedicle or lateral mass of a vertebra. With the shank 102 implanted into bone, the wing 116 of the base 104 can be rotated relative to the shank 102 and the receiver 106 to position the one or more auxiliary bone anchor openings 124 at a desired location. Various factors can be taken into consideration when positioning the wing 116 and auxiliary bone anchor openings 124 including, for example, placement of the shank 102, patient anatomy, other instrumentation, and surgical procedure requirements, such as, whether the bone into which the shank 102 engages is to be fused to one or more adjacent vertebrae.

One or more auxiliary bone anchors 108 can then be driven through the one or more corresponding auxiliary bone anchor openings 124 of the wing 116 into bone to supplement fixation of the bone anchor 100. As discussed in detail above, one or more of the auxiliary bone anchors 108 can be driven with an angled or biased trajectory relative to the central axis A1 of the bone anchor, the shank 102, and/or one or more other auxiliary bone anchor. A spinal rod can be placed within the rod-receiving recess 140 of the receiver member 106 and can be secured within the receiver member with a closure, for example, a set screw. The one or more auxiliary bone anchors 108 can be placed either before or after placement and/or securing of the spinal rod within the receiver member.

In any of the above embodiments or methods, the primary bone anchor can be omitted and the user can rely solely on the one or more auxiliary fixation features to secure the bone anchor. This can advantageously allow the position of the fixation to be completely offset from the receiver member, for example if an initially placed bone anchor needs to be removed due to improper positioning or inadequate purchase, or when the receiver member needs to be positioned over a location where a bone anchor cannot be inserted.

While the methods illustrated and described herein involve a bone anchor placed in the pedicle or lateral mass of vertebral bone, it will be appreciated that the systems and methods herein can be used in any bone, in non-bone tissue, or in non-living or non-tissue objects.

The auxiliary fixation members disclosed herein can be implanted in the same surgical procedure as the bone anchor, receiver member, and spinal rod, or, in the case of revision surgery, during a subsequent surgical procedure.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

As evident from the foregoing, in at least some embodiments, the systems and methods disclosed herein can provide enhanced fixation for a given surgical site, providing greater bone fixation strength at a given location without necessarily requiring moving the fixation to an additional vertebra or skipping/increasing the involved vertebral levels.

The bone anchor assemblies disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The method and devices described above relate to a spinal surgical application. While this is one contemplated use, the methods and devices of the present disclosure can be equally adapted for use in other areas of a patient's body, and can be used with any human or animal implant, in any of a variety of surgeries performed on humans or animals, and/or in fields unrelated to implants or surgery. As such, the devices described herein can be formed in a variety of sizes and materials appropriate for use in various areas of a patient's body. The systems and methods disclosed herein can be used in minimally-invasive surgery and/or open surgery.

Although specific embodiments are described above, it should be understood that numerous changes may be made within the spirit and scope of the concepts described. Accordingly, it is intended that this disclosure not be limited to the described embodiments, but that it have the full scope defined by the language of the following claims. All publications and references cited herein are expressly incorporated herein by reference in their entirety.

What is claimed is:

1. A bone anchor assembly, comprising:
   a bone anchor having a proximal head and a distal threaded shaft configured to engage bone;
   a receiver member having a pair of spaced apart arms for receiving a spinal fixation element therebetween, the receiver member having a first lumen formed therethrough;
   a base having a toroid body portion and a radially-extending protrusion with at least one auxiliary bone anchor opening to receive one or more auxiliary bone anchors therethrough, the base having a second lumen with a central longitudinal axis extending through the toroid body portion, the toroid body portion having an interior surface complementary to the proximal head such that the bone anchor can be retained within the toroid body portion and move polyaxially relative thereto,
   wherein the base is received within the receiver member such that the base is configured to rotate relative to one or more of the receiver member or the bone anchor.

2. The assembly of claim 1, further comprising an extension extending proximally from the toroid body portion, wherein at least a portion of the extension is received within a complementary portion in a distal end of the receiver member such that the toroid body portion extends distally from a distal surface of the receiver member.

3. The assembly of claim 2, wherein the extension is configured to engage a groove of the receiver member to retain the base within the receiver member.

4. The assembly of claim 2, wherein a portion of the extension extends distally from the receiver member such that the toroid body portion does not contact the receiver member.

5. The assembly of claim 1, wherein the base rotates about a longitudinal axis of the receiver member with relative movement of the base along the longitudinal axis is restricted.

6. The assembly of claim 1, further comprising a saddle received in the first lumen of the receiver member.

7. The assembly of claim 1, wherein the toroid body portion is configured to deform to allow passage of the proximal head into a recess formed in the toroid body portion.

8. The assembly of claim 1, wherein the one or more auxiliary bone anchor openings include a central axis that extends at an oblique angle relative to the central longitudinal axis.

9. The assembly of claim 8, wherein the central axis extends radially inward towards the central longitudinal axis or radially outward away from the central longitudinal axis.

10. The assembly of claim 1, wherein an outer surface of the pair of spaced apart arms includes one or more of a recess, dimple, notch, or projection to facilitate coupling of an instrument to the receiver member.

11. The assembly of claim 1, wherein a proximal facing surface of the toroid body portion contacts a distal-facing surface of the receiver member.

12. The assembly of claim 1, wherein the interior surface of the toroid body portion includes one or more of elastically deformable materials or elastic fingers forming a collet or other gripping structure.

13. A surgical method, comprising:
inserting a screw shank into a base such that a proximal head of the screw shank is seated within the base with a distal bone-engaging portion of the screw shank extending distally from the base, the base having a radially-extending portion including at least one auxiliary bone anchor opening and an extension extending proximally therefrom;
moving the screw shank polyaxially relative to the base;
implanting the screw shank in a bone of a patient;
inserting the extension through a distal opening of a receiver member and moving the extension proximally within the distal opening until a lip of the extension is captured within the receiver member; and
driving one or more auxiliary bone anchors through the at least one auxiliary bone anchor opening into bone to supplement fixation of the screw shank.

14. The method of claim 13, further comprising adjusting a position of the at least one auxiliary bone anchor opening relative to the receiver member and the one or more auxiliary bone anchors once the screw shank engages the bone.

15. The method of claim 13, wherein the one or more auxiliary bone anchors are driven through the at least one auxiliary bone anchor opening along a trajectory that extends at a transverse angle relative to a central axis of the at least one auxiliary bone anchor opening.

16. The method of claim 13, wherein the one or more auxiliary bone anchors are driven through the at least one auxiliary bone anchor opening with diverging or converging longitudinal axes relative to each other or relative to the screw shank.

17. The method of claim 13, wherein a spinal fixation rod is placed within the receiver member before driving one or more auxiliary bone anchors through the at least one auxiliary bone anchor opening.

18. The method of claim 13, wherein a spinal fixation rod is placed within the receiver member after driving one or more auxiliary bone anchors through the at least one auxiliary bone anchor opening.

19. The method of claim 1, wherein the screw shank passes proximally through the base to seat a proximal head of the screw shank into the base.

\* \* \* \* \*